United States Patent
Binabaji et al.

(10) Patent No.: US 11,447,547 B1
(45) Date of Patent: Sep. 20, 2022

(54) METHOD OF ANTIGEN-BINDING PROTEIN PRODUCTION

(71) Applicant: Amgen Inc., Thousand Oaks, CA (US)

(72) Inventors: Elaheh Binabaji, Los Angeles, CA (US); Chio Mui Chan, Los Angeles, CA (US); Hadley Krizner, Los Angeles, CA (US); Junfen Ma, Thousand Oaks, CA (US); Diana Woehle, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 580 days.

(21) Appl. No.: 16/219,871

(22) Filed: Dec. 13, 2018

Related U.S. Application Data

(60) Provisional application No. 62/598,015, filed on Dec. 13, 2017.

(51) Int. Cl.
| | |
|---|---|
| C07K 1/113 | (2006.01) |
| C07K 1/22 | (2006.01) |
| C07K 16/06 | (2006.01) |
| B01D 15/38 | (2006.01) |
| C07K 16/28 | (2006.01) |
| C07K 16/42 | (2006.01) |

(52) U.S. Cl.
CPC ...... *C07K 16/2809* (2013.01); *B01D 15/3828* (2013.01); *C07K 1/1133* (2013.01); *C07K 1/22* (2013.01); *C07K 16/065* (2013.01); *C07K 16/2878* (2013.01); *C07K 16/2896* (2013.01); *C07K 16/4283* (2013.01); *B01D 2015/3838* (2013.01)

(58) Field of Classification Search
CPC ...... C07K 1/1133; C07K 1/22; C07K 16/065; C07K 16/2878; C07K 16/2896
See application file for complete search history.

(56) References Cited

U.S. PATENT DOCUMENTS

| | | | |
|---|---|---|---|
| 5,072,720 | A | 12/1991 | Francis et al. |
| 5,169,936 | A | 12/1992 | Staples et al. |
| 6,933,370 | B2 | 8/2005 | Coffman et al. |
| 7,233,848 | B2 | 6/2007 | Braeuchle et al. |
| 7,306,934 | B2 | 12/2007 | Arora et al. |
| 7,825,223 | B2 | 11/2010 | Godavarti et al. |
| 7,928,205 | B2 | 4/2011 | Dillon et al. |
| 8,143,071 | B2 | 3/2012 | Gjerde |
| 8,440,799 | B2 | 5/2013 | Godavarti et al. |
| 8,574,869 | B2 | 11/2013 | Kao et al. |
| 8,617,531 | B2 | 12/2013 | Cox et al. |
| 2003/0212248 | A1 | 11/2003 | Furman |
| 2007/0071744 | A1* | 3/2007 | Munch ............. C07K 16/2803 424/133.1 |
| 2015/0225482 | A1* | 8/2015 | Song ................. C07K 16/22 530/387.3 |
| 2016/0347785 | A1 | 12/2016 | Hill et al. |

FOREIGN PATENT DOCUMENTS

| | | | |
|---|---|---|---|
| WO | WO-1994/015950 | | 7/1994 |
| WO | WO-2006/060083 A1 | | 6/2006 |
| WO | WO-2016016859 A1 * | 2/2016 | ......... C07K 16/2803 |

OTHER PUBLICATIONS

Michael Ostendorf, "Purification of monoclonal antibodies with BioPro SmartSep", Chromatography Today, Feb./Mar. 2017 (Year: 2017).*
Fahrner et al. "The optimal flow rate and column lenght for maximum production rate of protein A affinity chromatography" Bioprocess Engineering 21 (1999) 287-292 (Year: 1999).*
Chaderjian et al., Effect of copper sulfate on performance of a serum-free CHO cell culture process and the level of free thiol in the recombinant antibody expressed, *Biotechnol. Prog.* 21:550-3 (2005).
Choi et al., Reflectometric interference spectroscopy-based immunosensing using immobilized antibody via His-Tagged recombinant Protein A, *J. Bioscience and Bioeng.* 119:195-9 (2015).
Chung et al., Effects of antibody disulfide bond reduction on purification process performance and final drug substance stability, *Biotechnol. Bioeng.* 114:1264-74 (2017).
Liu et al., Recovery and purification process development for monoclonal antibody production, *mAbs* 2:480-99 (2010).
Martins et al., Chromatographic behaviour of monoclonal antibodies against wild-type amidase from Pseudomonas aeruginosa on immobilized metal chelates, *Chromatography.* 25:1327-37 (2011).
Nelson et al., Mechanism of immobilized Protein A binding to immunoglobulin G on nanosensor array surfaces, *Analytical Chem.* 87:8186-8193 (2015).
Patchornik, Purification of His-Tagged Proteins with [Desthiobiotin—BSA—EDTA] Conjugates Exhibiting Resistance to EDTA, *Bioconjugate Chem.* 19:673-679 (2008).
Rashid et al., Nickel-Salen supported paramagnetic nanoparticles for 6-His-target recombinant protein affinity purification, *J. Chromat.* 1490:47-53 (2017).
Seo et al., Regioselective Covalent Immobilization of Recombinant Antibody Binding Proteins A, G, and Protein L for Construction of Antibody Arrays, *J. Amer. Chem. Soc.* 135:8973-80 (2013).
Trexler-Schmidt et al., Identification and prevention of antibody disulfide bond reduction during cell culture manufacturing, *Biotechnol. Bioeng.* 106:452-61 (2010).
Wang et al., Investigation of antibody disulfide reduction and re-oxidation and impact to biological activities, *J. Pharm. Biomed. Anal.* 102:519-28 (2015).

* cited by examiner

*Primary Examiner* — Daniel E Kolker
*Assistant Examiner* — James L Rogers
(74) *Attorney, Agent, or Firm* — Marshall, Gerstein & Borun LLP

(57) ABSTRACT

The present disclosure relates to methods of re-oxidizing an antigen-binding protein.

35 Claims, 7 Drawing Sheets
Specification includes a Sequence Listing.

Figure 12

Target 1:

| | | |
|---|---|---|
| CL-1 | VH CDR1 | GYYMH |
| CL-1 | VH CDR2 | WINPNSGGTKYAQKFQG |
| CL-1 | VH CDR3 | DRITVAGTYYYGMDV |
| CL-1 | VL CDR1 | RASQGVNNWLA |
| CL-1 | VL CDR2 | TASSLQS |
| CL-1 | VL CDR3 | QQANSFPIT |
| CL-1 | VH | QVQLVQSGAEVKKPGASVKVSCKASGYTFTGYYMHWRQAPGQCLEWMGWINPNSGGTKYAQKFQGRVTMTRDTSISTAYME LSRLRSDDTAVYYCARDRITVAGTYYYYGMDVWGQGTTVTVSS |
| CL1 | VL | DIQMTQSPSSVSASVGDRVTITCRASQGVNNWLAWYQQKPGKAPKLLIYTASSLQSGVPSRFSGSGSGTDFTLTIRSLQPED FATYYCQQANSFPITFGCGTRLEIK |

TARGET 2

| | | |
|---|---|---|
| CL-2 | VH CDR1 | GYYMH |
| CL-2 | VH CDR2 | WINPNSGGTKYAQKFQG |
| CL-2 | VH CDR3 | DRITVAGTYYYGMDV |
| CL-2 | VL CDR1 | RASQGVNNWLA |
| CL-2 | VL CDR2 | TASSLQS |
| CL-2 | VL CDR3 | QQANSFPIT |
| CL-2 | VH | QVQMVQSGAEVKKHGASVKVSCKASGYTFTGYYMHWRQAPGQCLEWMGWINPNSGGTKYAQKFQGRVTMTRDTSISTAYME LSRLRSDDTAVYYCARDRITVAGTYYYYGMDVWGQGTTVTVSS |
| CL-2 | VL | DIQMTQSPSSVSASVGDRVTITCRASQGVNNWLAWYQQKPGKAPKLLIYTASSLQSGVPSRFSGSGSGTDFTLTIRSLQPED FATYYCQQANSFPITFGCGTRLEIK |

US 11,447,547 B1

SEQUENCE LISTING

<160> NUMBER OF SEQ ID NOS: 8

<210> SEQ ID NO 1
<211> LENGTH: 451
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Heavy Chain

<400> SEQUENCE: 1

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                 290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Light Chain

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
                35                  40                  45

Ala Thr Ser Asn Leu Ala Ser Gly Val Pro Val Arg Phe Ser Gly Ser
            50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
                130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
```

```
                180              185              190
Cys Glu Val Thr His Gln Gly Leu Ser Ser Pro Val Thr Lys Ser Phe
        195              200              205

Asn Arg Gly Glu Cys
    210

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR1

<400> SEQUENCE: 3

Ser Tyr Asn Met
1

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR2

<400> SEQUENCE: 4

Ala Ile Tyr Pro Gly Asn Gly Asp Thr Ser Tyr Asn Gln Lys Phe Lys
1               5                   10                  15
Gly

<210> SEQ ID NO 5
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: HC CDR3

<400> SEQUENCE: 5

Ser Thr Tyr Tyr Gly Gly Asp Trp Tyr Phe Asn
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR1

<400> SEQUENCE: 6

Arg Ala Ser Ser Ser Val Ser Tyr Ile His
1               5                   10

<210> SEQ ID NO 7
<211> LENGTH: 7
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: LC CDR2

<400> SEQUENCE: 7

Ala Thr Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: LC CDR3

<400> SEQUENCE: 8

Gln Gln Trp Thr Ser Asn Pro Pro Thr
1               5
```

METHOD OF ANTIGEN-BINDING PROTEIN PRODUCTION

This application claims priority to U.S. Provisional Patent Application No. 62/598,015, filed Dec. 13, 2017, which is incorporated by reference herein in its entirety.

FIELD OF THE INVENTION

The present disclosure relates to methods of re-oxidizing an antigen-binding protein.

SEQUENCE LISTING

This application contains, as a separate part of the disclosure, a sequence listing in computer-readable form (52267_SeqListing.txt; 7,673 bytes; created Dec. 13, 2018), which is incorporated by reference in its entirety.

BACKGROUND

Therapeutic antigen-binding proteins such as antibodies are currently used to treat millions of patients world-wide. Antigen-binding protein molecules are typically produced in mammalian cell culture systems and recovered using a standard series of filtration and chromatography steps (see, e.g., Liu et al., mAbs. 2(5): 480-499(2010)). The structure and stability of antigen-binding protein molecules depend heavily on the disulfide bonds that link the two heavy chains and the heavy and light chains in each antigen-binding protein molecule, however, during the production and purification process, one or more disulfide bonds can be reduced. Reduction of the inter-chain disulfide bonds weakens the structural integrity of the antigen-binding protein molecule and can lead to antigen-binding protein fragments (e.g., light chain, heavy chain, and their combinations) and/or antigen-binding protein aggregates, which impair the biological functions of the antigen-binding proteins and consequently, their therapeutic efficacy. Even if reduced molecules remain intact during the purification process via other forces (e.g., ionic, hydrophobic, hydrogen bonds, and Van der Waals), they may fragment during storage or in clinical use. Thus, there is a need for methods of re-oxidizing partially reduced antigen-binding protein molecules to produce stable and effective pharmaceutical formulations.

SUMMARY

The present disclosure is based on the discovery that subjecting an antigen-binding protein to a re-oxidizing solution comprising copper results in a significant reduction in reduced species of the antigen-binding protein. The term "reduced species" as used herein refers to both partially reduced (i.e., partial reduction of disulfide bond formation) and completely reduced species of the antigen-binding protein.

In one aspect, described herein is a method of re-oxidizing a therapeutic protein comprising at least one di-sulfide bridge, said method comprising: (a) subjecting a load composition comprising the therapeutic protein to an affinity chromatography column or membrane; and (b) washing the affinity chromatography column or membrane with a solution comprising a redox agent at a concentration of less than 1 mM.

In some embodiments, the redox agent is a transition metal, (3-mercaptoethanol, dithiothritol, tris (2-carboxyethyl)phosphine, cystamine, cysteamine or combinations thereof. In some embodiments, the transition metal is copper, iron, chromium, manganese, cobalt, nickel, zinc, scandium, titanium, vanadium, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, actinium, rutherfordium, dubnium, seaborgium, bohrium, hassium, meitnerium, darmstadtium, roentgenium and/or copernicium. In some embodiments, the transition metal is copper, iron, chromium, manganese, cobalt, nickel or zinc.

In some embodiments, the therapeutic protein is an antigen-binding protein.

In some embodiments, the affinity chromatography column is a Protein A affinity column or a Protein L affinity column.

In some embodiments, the transition metal is copper. In some embodiments, the copper in the solution is copper sulfate.

In some embodiments, the copper in the solution is present in an amount of no more than 250 µM. In some embodiments, the copper in the solution is present in an amount ranging from 2 µM to 250 µM. In some embodiments, the copper in the solution is present in an amount of approximately 40 µM.

In some embodiments, the conditions in step (b) comprise washing at room temperature. In some embodiments, the method further comprises incubating the load composition comprising the therapeutic protein at a temperature of approximately 2 to 8° C. before step (a).

In some embodiments, the load composition is incubated for 1-3 days at a temperature of approximately 2 to 8° C. and wherein the washing conditions in part (b) are conditions sufficient to achieve at least partial re-oxidation of the therapeutic protein.

In another aspect, described herein is a method of re-oxidizing a therapeutic protein comprising at least one reduced di-sulfide bridge, said method comprising: (a) incubating a load composition comprising the therapeutic protein at a temperature of approximately 2 to 8° C.; (b) subjecting the load composition to an affinity chromatography column or membrane; and (c) washing the affinity chromatography column or membrane with a solution comprising copper.

In some embodiments, the affinity chromatography column is a Protein A affinity column.

In some embodiments, the load composition is incubated for 1-3 days at a temperature of approximately 2 to 8° C. and wherein the washing conditions in the washing step are conditions sufficient to achieve at least partial re-oxidation of the therapeutic protein.

In some embodiments, wherein the copper in the solution is copper sulfate. In some embodiments, the copper in the solution is present in an amount of no more than 50 µM. In some embodiments, the copper in the re-oxidizing solution is present in an amount ranging from about 2 µM to about 50 µM. In some embodiments, the copper in the re-oxidizing solution is present in an amount of approximately 20 µM. In some embodiments, the copper in the solution is present in an amount of no more than 250 µM. In some embodiments, the copper in the re-oxidizing solution is present in an amount ranging from about 2 µM to about 250 µM. In some embodiments, the copper in the re-oxidizing solution is present in an amount of approximately 40 µM.

In some embodiments, the conditions in the washing step comprise washing at room temperature. In some embodiments, the conditions in the washing step comprise washing at a linear velocity of approximately 180-210 cm/hr. In some embodiments, the conditions in the washing step are sufficient to lower the amount of partially-reduced antigen-binding proteins to less than approximately 5% compared to more than approximately 15% in the load composition. In some embodiments, the conditions in the washing step are sufficient to lower the amount of partially-reduced antigen-binding proteins to less than approximately 4% compared to more than approximately 5% in the load composition.

In any of the embodiments described herein, the method optionally further comprises the step of freezing and thawing the load composition prior to the incubating step. In some embodiments, the method further comprises the step of recovering the therapeutic protein.

In some embodiments, the therapeutic protein is an antigen-binding protein. In some embodiments, the antigen-binding protein is an antibody (e.g., a recombinantly produced antibody). In some embodiments, the antibody is recombinantly produced in a Chinese Hamster Ovary (CHO) cell. In some embodiments, the antigen-binding protein is a Bi-specific T cell Engager (BiTE) molecule.

In some embodiments, the load composition is a harvested cell culture fluid (HCCF). In some embodiments, the antibody is an IgG1 or IgG2 antibody. In some embodiments, the antibody is an IgG1 antibody with a Kappa light chain. In some embodiments, the antibody is an IgG1 antibody with a Lambda light chain. In some embodiments, the antibody is selected from the group consisting of abciximab, adalimumab, alemtuzumab, basiliximab, belimumab, bevacizumab, brentuximab vedotin, canakinumab, cetuximab, certolizumab pegol, daclizumab, denosumab, eculizumab, efalizumab, gemtuzumab, golimumab, ibritumomab.

In some embodiments, the therapeutic protein binds an antigen selected from the group consisting of RANKL, tumor necrosis factor alpha, epidermal growth factor receptor, CD20, calcitonin gene-related peptide, sclerostin, and platelet glycoprotein IIb/IIIa.

In some embodiments, the BiTE molecule is an anti-CD33 and anti-CD3 BiTE molecule, anti-BCMA and anti-CD3 BiTE molecule, anti-FLT3 and anti-CD3 BiTE, anti-CD19 and anti-CD3 BiTE, anti-EGFRvIII and anti-CD3 BiTE molecule, anti-DLL3 and anti-CD3 BiTE, anti-CLDN18.2 and anti-CD3 BiTE molecule, anti-EpCAM and anti-CD-3 BiTE molecule, anti-CEA and anti-CD3 BiTE molecule, anti-PSMA and anti-CD3 BiTE molecule, blinatumomab (BLINCYTO), or solitomab.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE FIGURES

FIG. 12 provides the amino acid sequences of exemplary BiTE molecules that bind CLDN18.2.

DETAILED DESCRIPTION

Figure 1:
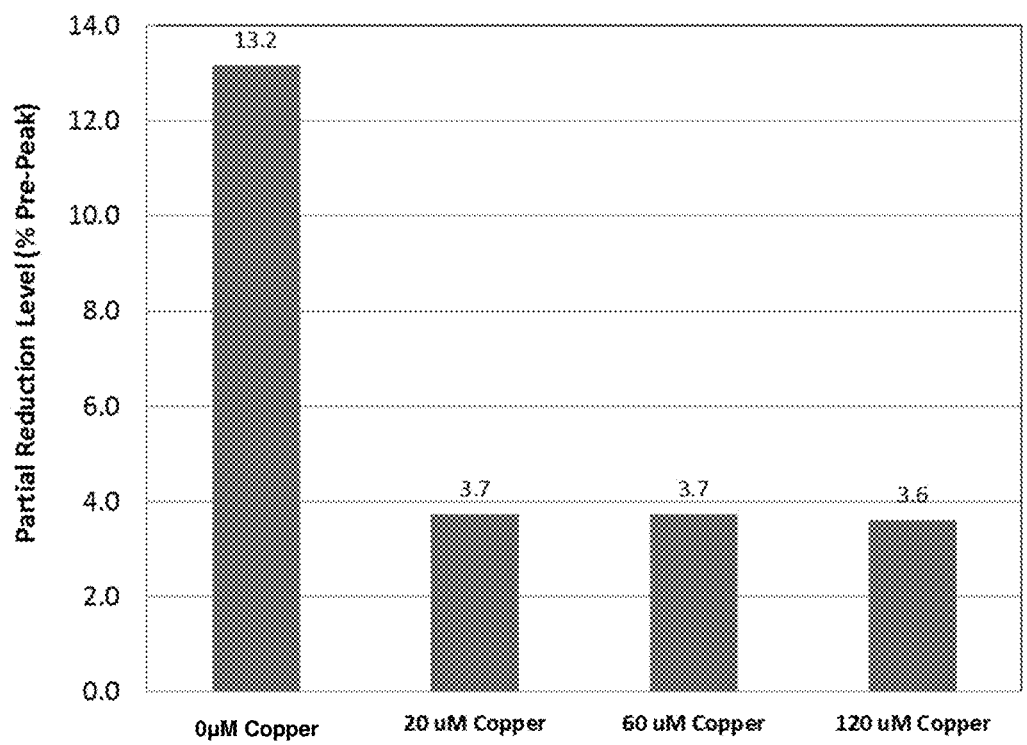
FIG. 1 shows the effect of copper wash concentration on level of partial reduction in ProA pool.

The present disclosure is based, at least in part, on the discovery that washing a therapeutic protein with a buffer comprising a redox agent (e.g., a transition metal such as copper) while the protein is bound to an affinity chromatography column results in re-oxidation of partially reduced species and therefore mitigates the level of partially-reduced product. In one aspect, the therapeutic protein is an antigen-binding protein as described herein. In another aspect, Protein A chromatography (ProA) is used according to the methods of the invention.

Techniques for Protein A chromatography are known in the art (e.g., Shukla et al., J Chromatogr A. 2007 Nov. 9; 1171(1-2):22-8. Epub 2007 Sep. 22; U.S. Pat. No. 8,263,750), and the process is routinely used to remove contaminants such as host cell protein, DNA, and viruses from a solution comprising antigen-binding protein molecules with an Fc region based on the affinity of Protein A for the Fc and/or Fab region of immunoglobulins. In some embodiments, a neutral or basic loading buffer (such as pH 7 to 8) is used to bind the antigen-binding protein onto the Protein A resin. In some embodiments, low pH is used to elute the antigen-binding protein from the Protein A resin, such as a pH between 3 and 5, such as 3 to 4, or 4 to 5.

In other embodiments, where, for example a different chromatography resin or membrane is employed, the pH of the loading and/or washing and/or eluting compositions range from 3 to 10. Other exemplary affinity or membrane chromatography methods include, but are not limited to, activated/functionalized chromatography, hydrophobic interaction chromatography, immunoaffinity, immobilized metal affinity chromatography, Protein L chromatography and Protein A/G chromatography.

In some embodiments, the method comprises optionally incubating a load composition comprising the therapeutic protein at a temperature of approximately 2 to 8° C. before subjecting the load composition to an affinity chromatography column or membrane. In some embodiments, the method comprises incubating the load composition for not more than three days. In some embodiments, the method comprises incubating the load compositions for one, two or three days. In various aspects, the load material, for example harvested cell culture fluid (HCCF) comprising an antigen-binding protein, is incubated for 5, 15, 30, or 45 minutes, or 1, 2, 3, 4, 5, 6, 7, 8, 9, 10, 11, 12 or 24 hours, or 2, 3, 4, 5, 6, 7, 8, 9 or 10 days prior to loading onto a column. The incubating step in the method is, in various embodiments, at a temperature of 1, 2, 3, 4, 5, 6, 7, 8, 9, 10, 11, 12, 13, 14, 15, 16, 17, 18, 19, or 20° C. In certain embodiments, the temperature is 2° C. to 8° C. In still another embodiment, the load material is optionally frozen and then thawed prior to loading onto a column.

The methods described herein include contacting a therapeutic protein with a redox agent. The term "redox agent" as used herein refers to any agent that facilitates formation of a disulfide bond in a therapeutic protein. Exemplary redox agents include, but are not limited to a transition metal, (3-mercaptoethanol, dithiothritol, tris (2-carboxyethyl)phosphine, cystamine and cysteamine. In some embodiments, the redox agent is an agent described in International Publication No. WO 2006/060083, the disclosure of which is incorporated herein by reference, such as chaotropic agents, cysteine and cystine, reduced and oxidized glutathione, dithiothreitol, 2-mercaptoethanol, hydrogen peroxide (oxidizer) and dithionitrobenzoate, and urea. Other agents such as divalent cations, including manganese, can also be used.

In some embodiments, the transition metal is copper, iron, chromium, manganese, cobalt, nickel, zinc, scandium, titanium, vanadium, yttrium, zirconium, niobium, molybdenum, technetium, ruthenium, rhodium, palladium, silver, cadmium, lanthanum, hafnium, tantalum, tungsten, rhenium, osmium, iridium, platinum, gold, mercury, actinium, rutherfordium, dubnium, seaborgium, bohrium, hassium, meitnerium, darmstadtium, roentgenium or copernicium. In some embodiments, the transition metal is copper, iron, chromium, manganese, cobalt, nickel or zinc.

In some embodiments, the redox agent is copper and this copper can be present in any compound comprising a copper ion. In some embodiments, the copper is present as copper sulfate pentahydrate. In some embodiments, the redox agent agent (e.g., copper) in the solution is present in an amount of no more than 250 µM, or in an amount ranging from about 2 µM to about 50 µM, or in an amount of approximately 20 µM. In some embodiments, the redox agent (e.g., copper) in the solution is present in an amount of more than 50 µM (e.g., ranging from about 50 µM to about 250 µM). In some embodiments, the redox agent (e.g., copper) in the solution is present in an amount of 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM, 200 µM, 205 µM, 210 µM, 210 µM, 220 µM, 225 µM, 230 µM, 235 µM, 240 µM, 245 µM, or 250 µM. In some embodiments, the redox agent (e.g., copper) in the solution is present in an amount ranging from 2 µM to 10 µM, or 5 µM to 10 µM, or 5 µM to 15 µM, or 10 µM to 20 µM, or 20 µM to 30 µM, or 30 µM to 40 µM or 40 µM to 50 µM, or 50 µM to 60 µM, 60 µM to 70 µM, 70 µM to 80 µM, 80 µM to 90 µM, 90 µM to 100 µM, 100 µM to 150 µM, 150 µM to 200 µM, 200 µM to 250 µM. In some embodiments, the redox agent (e.g., copper) in the solution is present in an amount of approximately 200 µM.

In some embodiments, when the redox agent is not copper, high concentrations are contemplated. For example, in some embodiments, when the redox agent is cystamine/cysteamine, the cystamine/cysteamine is present in an amount of at least 1 mM. In some embodiments, the redox agent (e.g., cystamine/cysteamine) in the solution is present in an amount of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 205 mM, 210 mM, 210 mM, 220 mM, 225 mM, 230 mM, 235 mM, 240 mM, 245 mM, or 250 mM. In some embodiments, the cystamine/cysteamine is present in an amount ranging from 1 mM to 10 mM, 2 mM to 10 mM, or 5 mM to 10 mM, or 5 mM to 15 mM, or 10 mM to 20 mM, or 20 mM to 30 mM, or 30 mM to 40 mM or 40 mM to 50 mM, or 50 mM to 60 mM, 60 mM to 70 mM, 70 mM to 80 mM, 80 mM to 90 mM, 90 mM to 100 mM, 100 mM to 150 mM, 150 mM to 200 mM, or 200 mM to 250 mM. In some embodiments, the solution comprises 1 mM cysteamine/4 mM cystamine.

In some embodiments, the conditions in the washing step comprise washing at room temperature. In various other embodiments, the conditions in the washing step as described herein comprise washing at a temperature of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. In still other embodiments, the load composition, which has been optionally frozen and thawed and/or optionally incubated at low temperature as described herein, is loaded onto a column, such as a Protein A column, under conditions that allow the load composition temperature to gradually increase to the desired washing temperature of the washing step described herein.

In some embodiments, the conditions in the washing step comprise washing at a linear velocity of 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 cm/hr. In some embodiments, the conditions in the washing step comprise washing at a linear velocity of approximately, 150-250, 160-220, 180-210, or 190-200 cm/hr.

Re-oxidation of therapeutic protein molecules (such as antigen-binding proteins comprising an Fc region, BiTE protein, fusion proteins, antibodies, antibody fragments or peptibodies) can be evidenced by a decrease in the amount (such as the total amount) or relative amount (e.g., percentage) of reduced (or partially-reduced) antigen-binding protein molecules, compared to the amount (such as the total amount) or relative amount (e.g., percentage) of reduced antigen-binding protein molecules observed prior to the optional incubating step described herein. In some embodiments, the conditions in the washing step are sufficient to lower the amount of reduced (or partially-reduced) antigen-binding proteins to less than approximately 5% compared to more than approximately 15% in the load composition. In some embodiments, the conditions in the washing step are sufficient to lower the amount of reduced (or partially-reduced) antigen-binding proteins to less than approximately 4% compared to more than approximately 5% in the load composition.

In some aspects, the percentage of reduced antigen-binding protein (such as an antigen-binding protein comprising an Fc region, BiTE molecule, an antibody, or a peptibody) molecules or reduced disulfide bonds in a solution comprising antigen-binding protein molecules is decreased by at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 45%, at least 50%, at least 55%, at least 60%, at least 65%, at least 70%, at least 75%, at least 80%, at least 85%, at least 90%, or more, following washing the antigen-binding protein (immobilized on a solid phase like Protein A resin) with a re-oxidizing solution comprising copper according to the disclosure, compared to the percentage of reduced antigen-binding protein molecules or reduced disulfide bonds observed prior to the washing step. In one aspect, the total amount of reduced antigen-binding protein molecules after washing the antigen-binding protein according to the disclosure with a re-oxidizing solution comprising copper is less than 10%, for example, less than 9%, less than 8%, less than 7%, less than 6%, less than 5%, less than 4%, less than 3%, less than 2%, or less than 1%, of the total amount of antigen-binding protein molecules. In one aspect, the total amount of reduced antigen-binding protein molecules after washing the antigen-binding protein according to the disclosure with a re-oxidizing solution comprising copper ranges from about 0% to about 4% (i.e., 0%, 1%, 1.5%, 2%, 2.5%, 3%, 3.5% or 4%). As another measure, the percentage of reduced antigen-binding protein molecules or reduced disulfide bonds is decreased by at least about 1.5 fold, for example, at least about 1.5-fold, at least about 2-fold, at least about 2.5-fold, at least about 3-fold, at least about 4-fold, at least about 5-fold, or more, after the antigen-binding protein molecules are washed with a re-oxidizing solution comprising copper as disclosed, compared to before the washing step.

In alternative embodiments, the therapeutic protein is contacted with the redox agent at a step of the manufacturing process that is downstream of affinity column. In such embodiments, the therapeutic protein is in a composition other than HCCF. For example, in some embodiments, the eluate from the affinity column comprising the therapeutic agent is collected and contacted with a redox agent (e.g., cystamine/cystamine) as described in Example 9.

Reduced (or partially-reduced) antigen-binding protein molecules can be measured, for example, by quantifying the amount of antigen-binding protein molecules in the load composition before and after contact with the Protein A column to assess the degree of inter-chain disulfide bond breakage. One method of identifying size variants and quantifying the amount of reduced (or partially reduced) antigen-binding protein molecules in a sample comprises using non-reduced capillary electrophoresis-sodium dodecyl sulfate (nrCE-SDS) to determine the percentage of pre-peak species corresponding to antigen-binding protein fragments (see, e.g., Guo et al., Electrophoresis. 29(12):2550-6 (2008)). Generally, non-reducing buffer is added to a sample. After incubation at high temperature, the samples are injected into a silica capillary. The separation is performed using a capillary electrophoresis sodium dodecyl sulfate (CE-SDS) gel, and effective voltage and detection is performed, for example, at 220 nm by UV absorbance. Other methods for measuring the purity of a composition of an antigen-binding protein, e.g., size exclusion chromatography (SEC), differentiate between protein aggregates and monomers, but do not distinguish between partially reduced and re-oxidized antigen-binding protein molecules in a sample and thus are not sufficient for use in the methods of the present disclosure.

The method further comprises, in some embodiments, the step of recovering the antigen-binding protein molecule from the column.

In another aspect, the antigen-binding protein molecules, following the wash with the re-oxidizing solution comprising copper and following one or more additional wash steps and elution steps (e.g., during Protein A chromatography), and optionally before or after one or more filtration steps, viral inactivation steps, chromatography steps and buffer exchange steps, are optionally contacted with a charged depth filter (International Patent Publication No. WO 2017/027861, the disclosure of which is incorporated herein by reference in its entirety). In some embodiments, after Protein A chromatography, the aqueous solution comprising antigen-binding protein molecules is incubated for at least 1, 2, 3, 4, 5, 6, 7, 8, 9, 10, 12, 15, 20, 24, or more hours before being contacted with a charged depth filter. In some embodiments, after protein A chromatography, the aqueous solution comprising antigen-binding protein molecules is incubated for between 2 and 10 hours (such as between 2 to 24 hours, 4 to 20 hours, or 4 to 10 hours) before being contacted with a charged depth filter. In another embodiment, the aqueous solution comprising antigen-binding protein molecules is first contacted with a charged depth filter and then afterwards subjected to Protein A chromatography. In some embodiments, after depth filtration, the aqueous solution comprising antigen-binding protein molecules is incubated for at least 1, 2, 3, 4, 5, 6, 7, 8, 9, 10, 12, 15, 20, 24, 32, 48 or more hours to promote re-oxidation before being subjected to chromatography. In some embodiments, after depth filtration, the aqueous solution comprising antigen-binding protein molecules is incubated for between 2 and 32 hours (such as between 12 to 24 hours, 24 to 48 hours, or 24 to 32 hours) before being subjected to chromatography.

Various parameters can be modified in the purification/re-oxidation methods described herein. Parameters include protein loading, temperature of operation, elution buffer choice, conductivity of the protein being loaded onto the column, bed heights (column height), linear velocities, and pH. Protein loading can be about 10 to about 200 g/L, 50 to about 200 g/L, about 55 to about 85 g/L, about 60 to about 80 g/L, about 65 to about 75 g/L, about 100 to about 200 g/L, about 100 to about 150 g/L, about 125 to about 175 g/L, about 150 to about 200 g/L, or about 90 to about 140 g/L. Temperature of operation on-column can be about 15° C. to about 25° C., or about 18° C. to about 22° C. The column height can be about 15 cm to about 35 cm, or about 20 cm to about 30 cm, or about 23 cm to about 27 cm. The linear velocity can be about 10 cm/hr to about 250 cm/hr, or about 120 cm/hr to about 220 cm/hr, about 125 cm/hr to about 165 cm/hr, or about 180 cm/hr to about 210 cm/hr. The pH can be about 5 to about 9, about 5 to about 7, about 7 to about 9, about 6 to about 8, about 5.5 to about 8.5, about 6.5 to about 8.5, about 5 to about 6, about 8 to about 9, about 7 to about 8, about 7 to about 7.5, or about 7.5 to about 8. In various cases, the pH is ±2 pH units of the pI of the protein of interest, or ±1 pH unit of the pI of the protein of interest, or ±0.5 pH units of the pI of the protein of interest. The conductivity of the protein being loaded onto the column can be about 10 to about 50 mS/cm, about 10 to about 20 mS/cm, about 15 to about 25 mS/cm, about 10 to about 30 mS/cm, about 10 to about 40 mS/cm, about 20 to about 50 mS/cm, about 30 to about 50 mS/cm, about 40 to about 50 mS/cm, about 20 to about 30 mS/cm, about 30 to about 40 mS/cm, or about 15 to about 30 mS/cm.

The length of the exposure time of wash to column is at least 15 minutes, preferably 25 minutes. In some embodiments, the length of exposure time of wash to column ranges from 15 minutes to 6 hours, to 12 hours, or to 24 hours, In some embodiments, the length of exposure time of wash to column is about 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 49 minutes, 50 minutes, 51 minutes, 52 minutes, 53 minutes, 54 minutes, 55 minutes, 56 minutes, 57 minutes, 58 minutes, 59 minutes, 1 hour, 2 hours, 3 hours, 4 hours, 5 hours, 6 hours, 7 hours, 8 hours, 9 hours, 10 hours, 11 hours 12 hours, 13 hours, 14 hours, 15 hours, 16 hours, 17 hours, 18 hours, 19 hours, 20 hours, 21 hours, 22 hours, 23 hours, 24 hours or longer. The length of wash to column can be calculated from linear velocity and column volume, as set forth in Example 2 below.

Therapeutic Proteins

Therapeutic proteins comprising one or more di-sulfide bridge are often susceptible to incorrect folding during the production and/or purification process. Misfolded proteins or aggregates and fragments must be removed to adequate levels due to their associated risks with immunogenicity and potential negative effects on drug efficacy. Alternatively, misfolded proteins resulting from reduced di-sulfide bonds may be "repaired" by subjecting the protein to conditions that enable correct protein folding (e.g., following re-oxidation of one or more reduced di-sulfide bonds).

In one aspect, therapeutic proteins that have been recombinantly produced and comprise at least one reduced di-sulfide bridge are contemplated by the disclosure. In one embodiment, the protein has one or more inter-di-sulfide bridges when properly folded. In one embodiment, the protein has one or more intra-di-sulfide bridges when properly folded. In one embodiment, the protein has one or more inter-di-sulfide bridges and one or more intra-di-sulfide bridges when properly folded. Assays for determining the presence of antibody protein molecules comprising properly folded disulfide bridges include, but are not limited to, non-reduced capillary electrophoresis-sodium dodecyl sulfate (nrCE-SDS), mass spectrometry (Gorman et al., Mass Spectrpm. Rev., 21:183-216, 2002), matrix-assisted laser desorption/ionization (MALDI) mass spectrometry (Yang et al., Top. Curr. Chem., 331:79-116, 2013), nanoliquid chromatography-tandem mass spectrometry (nanoLC-MS/MS) (Sokolowska et al., J. Lab. Autom., 17:408-416, 2012), and SDS-PAGE.

The term therapeutic protein as used herein refers to any therapeutic protein molecule comprising one or more di-sulfide bridges which exhibits biological activity that is associated with the therapeutic protein. In one embodiment of the present disclosure, the therapeutic protein molecule is a full-length protein. In various embodiments of the present disclosure, the therapeutic protein may be produced and purified from its natural source. Alternatively, according to the present disclosure, the term "recombinant therapeutic protein" includes any therapeutic protein obtained via recombinant DNA technology.

The therapeutic proteins include antigen-binding proteins. The term "antigen-binding protein" as used herein refers to a protein or polypeptide that comprises an antigen-binding region or antigen-binding portion that has a strong affinity for another molecule to which it binds (antigen). Antigen-binding proteins encompass antibodies, peptibodies, antibody fragments, antibody derivatives, antibody analogs, fusion proteins (including single-chain variable fragments (scFvs) and double-chain (divalent) scFvs, trivalent and tetravalent, BiTEs, etc.),), and antigen receptors including chimeric antigen receptors (CARs).

In some embodiments, the antigen-binding protein is an antibody. As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. The constant region allows the antibody to recruit cells and molecules of the immune system. The variable region is made of the N-terminal regions of each light chain and heavy chain, while the constant region is made of the C-terminal portions of each of the heavy and light chains. (Janeway et al., "Structure of the Antibody Molecule and the Immunoglobulin Genes", Immunobiology: The Immune System in Health and Disease, 4th ed. Elsevier Science Ltd./Garland Publishing, (1999)).

The general structure and properties of CDRs of antibodies have been described in the art. Briefly, in an antibody scaffold, the CDRs are embedded within a framework in the heavy and light chain variable region where they constitute the regions largely responsible for antigen binding and recognition. A variable region comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the invention include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4. IgG1 antibodies are particularly susceptible to reduction of di-sulfide bonds and, as a result, represent one preferred embodiment of the disclosure.

The antibody may be a monoclonal antibody or a polyclonal antibody. In some embodiments, the antibody comprises a sequence that is substantially similar to a naturally-occurring antibody produced by a mammal, e.g., mouse, rabbit, goat, horse, chicken, hamster, human, and the like. In this regard, the antibody may be considered as a mammalian antibody, e.g., a mouse antibody, rabbit antibody, goat antibody, horse antibody, chicken antibody, hamster antibody, human antibody, and the like. In certain aspects, the monoclonal antibody is a human antibody. In certain aspects, the monoclonal antibody is a chimeric antibody or a humanized antibody. The term "chimeric antibody" is used herein to refer to an antibody containing constant domains from one species and the variable domains from a second, or more generally, containing stretches of amino acid sequence from at least two species. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence.

Antigen-binding proteins include those based on antibody fragments, e.g., scFvs, Fabs and VHH/VH, which retain full antigen-binding capacity. The smallest antigen-binding fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment. Both scFv and Fab are widely used fragments that can be easily produced in prokaryotic hosts. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

In some embodiments, the antigen binding protein comprises any one of an scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate.

Other antigen binding proteins include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

The antigen binding protein may be an antibody binding protein in monomeric form, or polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

Advantageously, the methods are not limited to the antigen-specificity of the antibody. Accordingly, the antibody has any binding specificity for virtually any antigen. In exemplary aspects, the antibody binds to a hormone, growth factor, cytokine, a cell-surface receptor, or any ligand thereof. In exemplary aspects, the antibody binds to a protein expressed on the cell surface of an immune cell. In some embodiments, the antibody binds to a cluster of differentiation molecule selected from the group consisting of: CD1a, CD1b, CD1c, CD1d, CD2, CD3, CD4, CD5, CD6, CD7, CD8, CD9, CD10, CD11A, CD11B, CD11C, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45RO, CD45RA, CD45RB, CD46, CD47, CD48, CD49a, CD49b, CD49c, CD49d, CD49e, CD49f, LD50, CD51, CD52, CD53, CD54, CD55, CD56, CD57, CD58, CD59, CDw60, CD61, CD62E, CD62L, CD62P, CD63, CD64, CD65, CD66a, CD66b, CD66c, CD66d, CD66e, CD66f, CD68, CD69, CD70, CD71, CD72, CD73, CD74, CD75, CD76, CD79α, CD79β, CD80, CD81, CD82, CD83, CDw84, CD85, CD86, CD87, CD88, CD89, CD90, CD91, CDw92, CD93, CD94, CD95, CD96, CD97, CD98, CD99, CD100, CD101, CD102, CD103, CD104, CD105, CD106, CD107a, CD107b, CDw108, CD109, CD114, CD 115, CD116, CD117, CD118, CD119, CD120a, CD120b, CD121a, CDw121b, CD122, CD123, CD124, CD125, CD126, CD127, CDw128, CD129, CD130, CDw131, CD132, CD134, CD135, CDw136, CDw137, CD138, CD139, CD140a, CD140b, CD141, CD142, CD143, CD144, CD145, CD146, CD147, CD148, CD150, CD151, CD152, CD153, CD154, CD155, CD156, CD157, CD158a, CD158b, CD161, CD162, CD163, CD164, CD165, CD166, and CD182.

In some embodiments, the antigen binding protein, antibody or therapeutic protein is one of those described in U.S. Pat. No. 7,947,809 and U.S. Patent Application Publication No. 20090041784 (glucagon receptor), U.S. Pat. Nos. 7,939,070, 7,833,527, 7,767,206, and 7,786,284 (IL-17 receptor A), U.S. Pat. Nos. 7,872,106 and 7,592,429 (Sclerostin), U.S. Pat. Nos. 7,871,611, 7,815,907, 7,037,498, 7,700,742, and U.S. Patent Application Publication No. 20100255538 (IGF-1 receptor), U.S. Pat. No. 7,868,140 (B7RP1), U.S. Pat. No. 7,807,159 and U.S. Patent Application Publication No. 20110091455 (myostatin), U.S. Pat. Nos. 7,736,644, 7,628,986, 7,524,496, and U.S. Patent Application Publication No. 20100111979 (deletion mutants of epidermal growth factor receptor), U.S. Pat. No. 7,728,110 (SARS coronavirus), U.S. Pat. No. 7,718,776 and U.S. Patent Application Publication No. 20100209435 (OPGL), U.S. Pat. Nos. 7,658,924 and 7,521,053 (Angiopoietin-2), U.S. Pat. Nos. 7,601,818, 7,795,413, U.S. Patent Application Publication No. 20090155274, U.S. Patent Application Publication No. 20110040076 (NGF), U.S. Pat. No. 7,579,186 (TGF-β type II receptor), U.S. Pat. No. 7,541,438 (connective tissue growth factor), U.S. Pat. No. 7,438,910 (IL1-R1), U.S. Pat. No. 7,423,128 (properdin), U.S. Pat. Nos. 7,411,057, 7,824,679, 7,109,003, 6,682,736, 7,132,281, and 7,807,797 (CTLA-4), U.S. Pat. Nos. 7,084,257, 7,790,859, 7,335,743, 7,084,257, and U.S. Patent Application Publication No. 20110045537 (interferon-gamma), U.S. Pat. No. 7,932,372 (MAdCAM), U.S. Pat. No. 7,906,625, U.S. Patent Application Publication No. 20080292639, and U.S. Patent Application Publication No. 20110044986 (amyloid), U.S. Pat. Nos. 7,815,907 and 7,700,742 (insulin-like growth factor I), U.S. Pat. Nos. 7,566,772 and 7,964,193 (interleukin-1β), U.S. Pat. Nos. 7,563,442, 7,288,251, 7,338,660, 7,626,012, 7,618,633, and U.S. Patent Application Publication No. 20100098694 (CD40), U.S. Pat. No. 7,498,420 (c-Met), U.S. Pat. Nos. 7,326,414, 7,592,430, and 7,728,113 (M-CSF), U.S. Pat. Nos. 6,924,360, 7,067,131, and 7,090,844 (MUC18), U.S. Pat. Nos. 6,235,883, 7,807,798, and U.S. Patent Application Publication No. 20100305307 (epidermal growth factor receptor), U.S. Pat. Nos. 6,716,587, 7,872,113, 7,465,450, 7,186,809, 7,317,090, and 7,638,606 (interleukin-4 receptor), U.S. Patent Application Publication No. 20110135657 (BETA-KLOTHO), U.S. Pat. Nos. 7,887,799 and 7,879,323 (fibroblast growth factor-like polypeptides), U.S. Pat. No. 7,867,494 (IgE), U.S. Patent Application Publication No. 20100254975 (ALPHA-4 BETA-7), U.S. Patent Application Publication No. 20100197005 and U.S. Pat. No. 7,537,762 (ACTIVIN RECEPTOR-LIKE KINASE-1), U.S. Pat. No. 7,585,500 and U.S. Patent Application Publication No. 20100047253 (IL-13), U.S. Patent Application Publication No. 20090263383 and U.S. Pat. No. 7,449,555 (CD148), U.S. Patent Application Publication No. 20090234106 (ACTIVIN A), U.S. Patent Application Publication No. 20090226447 (angiopoietin-1 and angiopoietin-2), U.S. Patent Application Publication No. 20090191212 (Angiopoietin-2), U.S. Patent Application Publication No. 20090155164 (C-FMS), U.S. Pat. No. 7,537,762 (activin receptor-like kinase-1), U.S. Pat. No. 7,371,381 (galanin), U.S. Patent Application Publication No. 20070196376 (INSULIN-LIKE GROWTH FACTORS), U.S. Pat. Nos. 7,267,960 and 7,741,115 (LDCAM), U.S. Pat. No. 7,265,212 (CD45RB), U.S. Pat. No. 7,709,611, U.S. Patent Application Publication No. 20060127393 and U.S. Patent Application Publication No. 20100040619 (DKK1), U.S. Pat. No. 7,807,795, U.S. Patent Application Publication No. 20030103978 and U.S. Pat. No. 7,923,008 (osteoprotegerin), U.S. Patent Application Publication No. 20090208489 (OV064), U.S. Patent Application Publication No. 20080286284 (PSMA), U.S. Pat. No. 7,888,482, U.S. Patent Application Publication No. 20110165171, and U.S. Patent Application Publication No. 20110059063 (PAR2), U.S. Patent Application Publication No. 20110150888 (HEPCIDIN), U.S. Pat. No. 7,939,640 (B7L-1), U.S. Pat. No. 7,915,391 (c-Kit), U.S. Pat. Nos. 7,807,796, 7,193,058, and U.S. Pat. No. 7,427,669 (ULBP), U.S. Pat. Nos. 7,786,271, 7,304,144, and U.S. Patent Application Publication No. 20090238823 (TSLP), U.S. Pat. No. 7,767,793 (SIGIRR), U.S. Pat. No. 7,705,130 (HER-3), U.S. Pat. No. 7,704,501 (ataxin-1-like polypeptide), U.S. Pat. Nos. 7,695,948 and 7,199,224 (TNF-α converting enzyme), U.S. Patent Application Publication No. 20090234106 (ACTIVIN A), U.S. Patent Application Publication No. 20090214559 and U.S. Pat. No. 7,438,910 (IL1-R1), U.S. Pat. No. 7,579,186 (TGF-β type II receptor), U.S. Pat. No. 7,569,387 (TNF receptor-like molecules), U.S. Pat. No. 7,541,438, (connective tissue growth factor), U.S. Pat. No. 7,521,048 (TRAIL receptor-2), U.S. Pat. Nos. 6,319,499, 7,081,523, and U.S. Patent Application Publication No. 20080182976 (erythropoietin receptor), U.S. Patent Application Publication No. 20080166352 and U.S. Pat. No. 7,435,796 (B7RP1), U.S. Pat. No. 7,423,128 (properdin), U.S. Pat. Nos. 7,422,742 and 7,141,653 (interleukin-5), U.S. Pat. Nos. 6,740,522 and 7,411,050 (RANKL), U.S. Pat. No. 7,378,091 (carbonic anhydrase IX (CA IX) tumor antigen), U.S. Pat. Nos. 7,318,925 and 7,288,253 (parathyroid hormone), U.S. Pat. No. 7,285,269 (TNF), U.S. Pat. Nos. 6,692,740 and 7,270,817 (ACPL), U.S. Pat. No. 7,202,343 (monocyte chemo-attractant protein-1), U.S. Pat. No. 7,144,731 (SCF), U.S. Pat. Nos. 6,355,779 and 7,138,500 (4-1BB), U.S. Pat. No. 7,135,174 (PDGFD), U.S. Pat. Nos. 6,630,143 and 7,045,128 (Flt-3 ligand), U.S. Pat. No. 6,849,450 (metalloproteinase inhibitor), U.S. Pat. No. 6,596,852 (LERK-5), U.S. Pat. No. 6,232,447 (LERK-6), U.S. Pat. No. 6,500,429 (brain-derived neurotrophic factor), U.S. Pat. No. 6,184,359 (epithelium-derived T-cell factor), U.S. Pat. No. 6,143,874 (neurotrophic factor NNT-1), U.S. Patent Application Publication No. 20110027287 (PROPROTEIN CONVERTASE SUBTILISIN KEXIN TYPE 9 (PCSK9)), U.S. Patent Application Publication No. 20110014201 (IL-18 RECEPTOR), and U.S. Patent Application Publication No. 20090155164 (C-FMS). The above patents and published patent applications are incorporated herein by reference in their entirety for purposes of their disclosure of variable domain polypeptides, variable domain encoding nucleic acids, host cells, vectors, methods of making polypeptides encoding said variable domains, pharmaceutical compositions, and methods of treating diseases associated with the respective target of the variable domain-containing antigen binding protein or antibody.

In some embodiments, the antibody is selected from the group consisting of Muromonab-CD3 (product marketed with the brand name Orthoclone Okt3®), Abciximab (product marketed with the brand name Reopro®.), Rituximab (product marketed with the brand name MabThera®, Rituxan®) (U.S. Pat. No. 5,843,439), Basiliximab (product marketed with the brand name Simulect®), Daclizumab (product marketed with the brand name Zenapax®), Palivizumab (product marketed with the brand name Synagis®), Infliximab (product marketed with the brand name Remicade®), Trastuzumab (product marketed with the brand name Herceptin®), Alemtuzumab (product marketed with the brand name MabCampath®, Campath-1H®), Adalimumab (product marketed with the brand name Humira®), Tositumomab-I131 (product marketed with the brand name Bexxar®), Efalizumab (product marketed with the brand name Raptiva®), Cetuximab (product marketed with the brand name Erbitux®), l'Ibritumomab tiuxetan (product marketed with the brand name Zevalin®), l'Omalizumab (product marketed with the brand name Xolair®), Bevacizumab (product marketed with the brand name Avastin®), Natalizumab (product marketed with the brand name Tysabri®), Ranibizumab (product marketed with the brand name Lucentis®), Panitumumab (product marketed with the brand name Vectibix®), l'Eculizumab (product marketed with the brand name Soliris®), Certolizumab pegol (product marketed with the brand name Cimzia®), Golimumab (product marketed with the brand name Simponi®), Canakinumab (product marketed with the brand name Ilaris®), Catumaxomab (product marketed with the brand name Removab®), Ustekinumab (product marketed with the brand name Stelara®), Tocilizumab (product marketed with the brand name RoActemra®, Actemra®), Ofatumumab (product marketed with the brand name Arzerra®), Denosumab (product marketed with the brand name Prolia®), Belimumab (product marketed with the brand name Benlysta®), Raxibacumab, Ipilimumab (product marketed with the brand name Yervoy®), and Pertuzumab (product marketed with the brand name Perjeta®). In exemplary embodiments, the antibody is one of anti-TNF alpha antibodies such as adalimumab, infliximab, etanercept, golimumab, and certolizumab pegol; anti-IL1.beta. antibodies such as canakinumab; anti-IL12/23 (p40) antibodies such as ustekinumab and briakinumab; and anti-IL2R antibodies, such as daclizumab. Examples of suitable anti-cancer antibodies include, but are not limited to, anti-BAFF antibodies such as belimumab; anti-CD20 antibodies such as rituximab; anti-CD22 antibodies such as epratuzumab; anti-CD25 antibodies such as daclizumab; anti-CD30 antibodies such as iratumumab, anti-CD33 antibodies such as gemtuzumab, anti-CD52 antibodies such as alemtuzumab; anti-CD152 antibodies such as ipilimumab; anti-EGFR antibodies such as cetuximab; anti-HER2 antibodies such as trastuzumab and pertuzumab; anti-IL6 antibodies such as siltuximab; and anti-VEGF antibodies such as bevacizumab; anti-IL6 receptor antibodies such as tocilizumab.

Antigen-binding proteins directed against (human) CD3 or specifically against CD3 epsilon are known in the art, and their CDRs, VH and VL sequences can serve as a basis for the second binding domain of the antibody construct of the invention. For example, Kung et al. reported in 1979 the development of OKT3 (Ortho Kung T3), the first mAb recognizing CD3 (specifically, the epsilon chain of CD3) on human T cells. OKT3 (muromonab) was the first monoclonal antibody of murine origin to become available for therapy in humans. Newer anti-CD3 monoclonal antibodies include otelixizumab (TRX4), teplizumab (MGA031), foralumab and visilizumab, all targeting the epsilon chain of CD3. Bispecific antibody constructs directed against a (cancer) target and CD3 are also being developed and (pre-) clinically tested, and their CD3 binding domain (CDRs, VH, VL) may serve as a basis for the second binding domain of the antibody construct of the invention. Examples include, but are not limited to, Blinatumomab, Solitomab (MT110, AMG 110), Catumaxomab, Duvortuxizumab, Ertumaxomab, Mosunetuzumab, FBTA05 (Bi20, TPBs05), CEA-TCB (RG7802, R06958688), AFM11, and MGD006 (S80880). Other examples of CD3 binding domains are disclosed e.g. in U.S. Pat. No. 7,994,289 B2, U.S. Pat. No. 7,728,114 B2, U.S. Pat. No. 7,381,803 B1, U.S. Pat. No. 6,706,265 B1.

In some embodiments, the antibody comprises a heavy chain that is at least 90%, for example, at least 92%, at least 95%, at least 97%, or at least 99%, identical to SEQ ID NO: 1, and a light chain that is at least 90%, for example, at least 92%, at least 95%, at least 96%, at least 97%, or at least 99%, identical to SEQ ID NO: 2; or comprises 1, 2, 3, 4, 5, or 6 of the CDRs set forth in SEQ ID NOs: 3-8. In some embodiments, the antibody comprises all 6 CDRs set forth in SEQ ID NOs: 3-8.

Antigen-binding proteins described herein encompass all of the foregoing and further include variants that retain all of the heavy chain CDRs thereof, and/or all of the light chain CDRs thereof, and comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of an antigen-binding protein, as illustrated above, particularly a pharmaceutical binding protein, such as a GenBank or other reference sequence of a reference protein. Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

Particularly preferred variants in this regard have 50% to 150% of the activity of the aforementioned reference antigen-binding protein, particularly highly preferred embodiments in this regard have 60% to 125% of the activity of the reference antigen-binding protein, yet more highly preferred embodiments have 75% to 110% of the activity of the reference antigen-binding protein, still more highly preferred embodiments have 85% to 125% the activity of the reference, still more highly preferred embodiments have 90% to 110% of the activity of the reference.

In some embodiments, the antigen-binding protein is a bispecific T cell engager (BiTE) molecule. BiTE molecules are a bispecific construct or bispecific fusion protein comprising two antibody binding domains (or targeting regions) linked together.

The term "binding domain" in regards to a BiTE molecule refers to a domain which (specifically) binds to/interacts with/recognizes a given target epitope or a given target site on the target molecules (antigens). The structure and function of the first binding domain (recognizing the tumor cell antigen), and preferably also the structure and/or function of the second binding domain (cytotoxic T cell antigen), is/are based on the structure and/or function of an antibody, e.g. of a full-length or whole immunoglobulin molecule.

For example, the BiTE molecule comprises a first binding domain characterized by the presence of three light chain CDRs (i.e. CDR1, CDR2 and CDR3 of the VL region) and three heavy chain CDRs (i.e. CDR1, CDR2 and CDR3 of the VH region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region). It is envisaged that the first and/or second binding domain is produced by or obtainable by phage-display or library screening methods rather than by grafting CDR sequences from a pre-existing (monoclonal) antibody into a scaffold.

Exemplary BiTE molecules include anti-CD33 and anti-CD3 BiTE molecule, anti-BCMA and anti-CD3 BiTE molecule (International Publication Nos. WO 2012/066058, WO 2013/072415, WO 2013/072406), anti-FLT3 and anti-CD3 BiTE, anti-CD19 and anti-CD3 BiTE (U.S. Pat. Nos. 7,235,641; 7,575,923; 7,635,472; 8,247,194 and U.S. Patent Publication Nos. 2012/0328618 and 2012/0323247), anti-EGFRvIII and anti-CD3 BiTE molecule, anti-DLL3 and anti-CD3 BiTE, anti-CLDN18.2 and anti-CD3 BiTE molecule, anti-EpCAM and anti-CD-3 BiTE molecule, anti-CEA and anti-CD3 BiTE molecule, anti-PSMA and anti-CD3 BiTE molecule, blinatumomab (BLINCYTO), and solitomab. Exemplary amino acid sequences for the anti-CLDN18.2 binding domain are provided in FIG. 12.

Formulations comprising a therapeutic protein, e.g., an antigen-binding protein, prepared according to the methods described herein are also contemplated. Many reagents and methods conventionally employed for the formulation of pharmaceutical antigen-binding protein formulations can be used for the formulations in accordance with various aspects and preferred embodiments of the disclosure. In accordance therewith, many methods and ingredients for formulating and using pharmaceuticals that are well-known and routine in the pertinent arts can be used in designing, making, and using formulations in accordance with various aspects and preferred embodiments of the disclosure relating thereto.

The present disclosure will be more readily understood by reference to the following Examples, which are provided by way of illustration and are not intended to be limiting.

EXAMPLES

Example 1—Materials and Methods

Abbreviations:
ProA: Protein A
nProA: Neutralized Protein A pool
nVIP: Neutralized viral inactivation pool
FVIP: Filtered neutralized viral inactivation pool
CV: Column volume
SE-HPLC: Size exclusion-high performance liquid chromatography
nrCE-SDS: non-reduced capillary electrophoresis
rCE-SDS: reduced capillary electrophoresis
HMW: High molecular weight species
LMW: Low molecular weight species
LC: Light chain
HC: Heavy chain
ppm: Parts per million
ppb: Parts per billion
mg/mLr: milligram of proteins/milliliter of resin Unless otherwise specified, the following are applicable to all chromatography experiments:

MabSelect SuRe resin was used for all the experiments and experiments were performed on one of two ProA columns of varying diameters. ProA columns were packed to 25±2 cm bed height and were tested for integrity. pH and conductivity were monitored using in-line probes.

Load material was harvested cell culture fluid (HCCF). In most cases fresh HCCF (no freeze-thaw) was used but in few cases where frozen HCCF was used the material was thawed by placing it in room temperature water bath.

Operation was at room temperature. HCCF was loaded to column at room temperature however in some cases the HCCF was at cold temperature as it was not brought to room temperature before loading on ProA (specifically in some cases where HCCF was fresh and kept in cold 2-8° C. prior to loading on ProA).

Copper sulfate pentahydrate was used. A stock solution of 0.0075 M copper was prepared by dissolving adequate amount of copper sulfate penta hydrate into DI water and filtered using Millipore Express PLUS 0.22 μm hydrophilic polyethersulfone (PES) membrane filter.

For on column re-oxidation experiments, Wash 1 solution with desired concentration of copper was prepared by spiking adequate volume of this stock solution into ProA equilibration buffer.

For all ProA pool samples, part of ProA pool was first neutralized to pH 5 using 2 M Tris solution and then samples were taken from this nProA.

For all of the samples for nrCE-SDS assay 3 separate samples (2 reserves) were taken and were frozen at −70° C. right away.

Example 2—Design and Optimization of the Copper Wash

The copper wash at the concentration described above in Example 1 is applied to a MabSelect column described above at a linear velocity of 180 cm/hr for 4 column volumes.

The length of the exposure time to wash is 25 minutes, controlled by the linear velocity of flow during wash step and the length of the wash step (i.e. number of column volumes for the wash). The result of initial experiments are shown as third group of data in FIG. 1 suggesting that copper addition during ProA wash 1 is also effective in reducing the level of partial reduction.

Although load material used for copper wash experiments had an original level of partial reduction (prior to copper wash) of 16.1%, after one freeze (at −70° C.) and thaw step reduced to 5.7%. Nevertheless, addition of 2 μM copper in the wash buffer was effective in bringing the level of partial reduction down to 3.8% for this material. It was surprising that the copper wash was able to further bring down the level of partial reduction even when the original level of partial reduction was at low levels.

Experiments were also performed to investigate effect of copper wash at higher level (60 μM and 120 μM copper) in further lowering down partial reduction levels and the results are shown in FIG. 1. This data shows that copper wash with even higher concentrations of copper is only as effective as 20 μM copper wash for the Ab-A compositions tested proving that the column is saturated with copper and all the bound protein is exposed to copper for re-oxidation.

Figure 2:
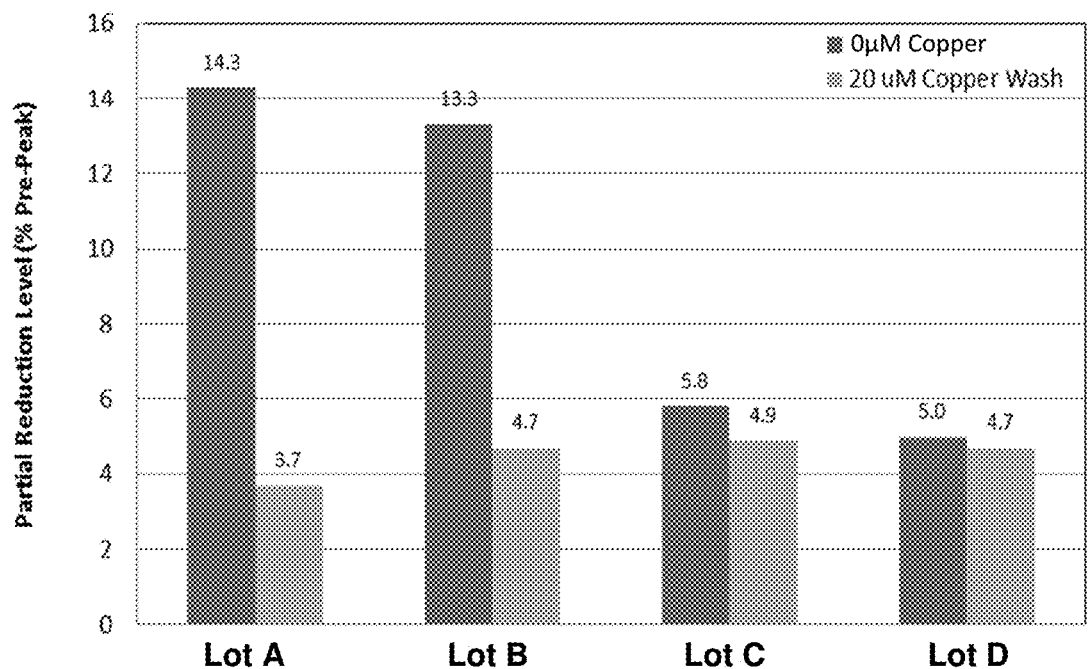
FIG. 2 shows the effect of copper wash (20 µM) during ProA on level of partial reduction in ProA pool.

FIG. 2 shows the effect of using a 20 μM copper wash during ProA wash 1 in reducing partial reduction level for 4 different load materials (Lot A, Lot B, Lot C, and Lot D) with different initial levels of partial reduction. In all cases, application of the copper wash was effective in bringing down the level of partial reduction to a degree that partial reduction was decreased from 14.3% down to 3.7%.

Figure 3:
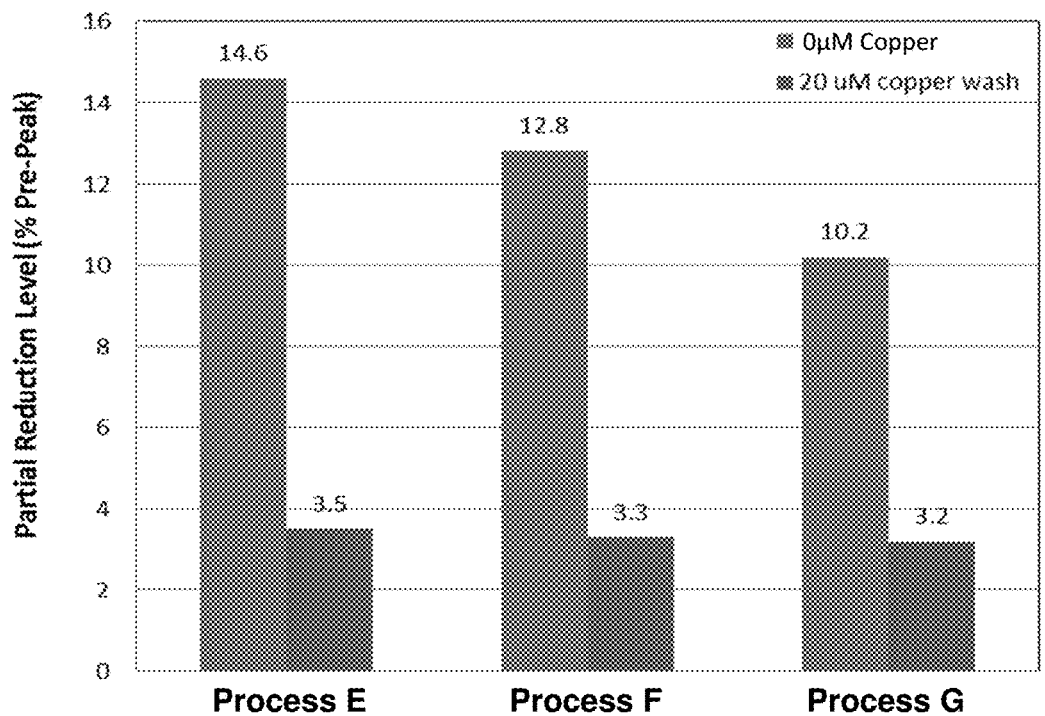
FIG. 3 shows the effect of copper wash (20 µM) during ProA on level of partial reduction in ProA pool.

Experiments were also repeated with material from one bioreactor lot divided into different harvest conditions. In the production of Lot E, there was no oxygen added during the harvest process. In the production of Lot F, there was no oxygen added, and the harvested cell culture fluid was transferred to a holding tank through a long transfer line. In the production of Lot G, there was no oxygen added, and the harvested cell culture fluid was transferred through a long transfer line to a holding tank contain Protein A equilibration buffer (a neutral pH buffer with sodium chloride) The results shown in FIG. 3 showed that regardless of how the HCCF was previously treated, the copper wash was effective in bringing down the level of partial reduction to less than 4%. Results from these experiments show that even at initial partial reduction level of 14.6% by using the copper wash a partial reduction level of less than 3% was achieved.

Partial reduction level for Ab A can be lowered down to less than 4% in ProA pool when copper wash is used for on column re-oxidation after ProA load. Also, the summary of all the data indicate that while partial reduction is mitigated using the copper wash the lowest level achieved was around 3% and neither increasing level of copper nor the exposure time to copper was able to further lower the partial reduction percentage.

Example 3—Effect of HCCF Temperature Control on Copper Wash Effectiveness

Figure 4:
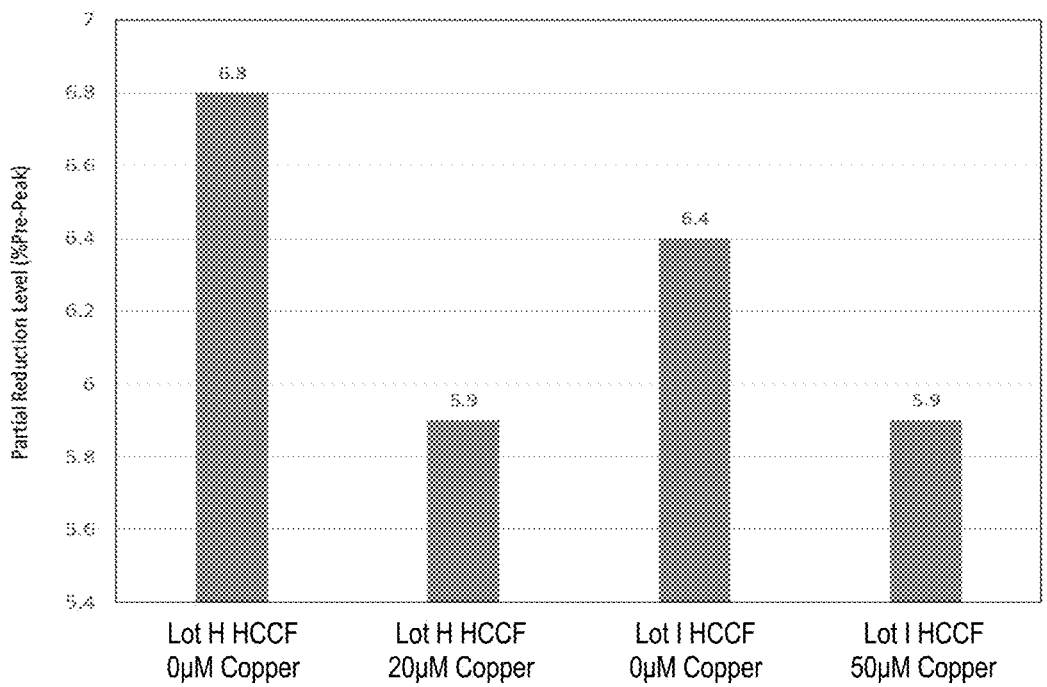
FIG. 4 shows the effect of harvested cell culture fluid (HCCF) hold temperature on mitigation of partial reduction using copper wash.

In the above experiments, the harvested cell culture fluid (HCCF) materials used was collected at 2-8° C. Two experiments were performed with two lots of HCCF material (Lot H and Lot I) collected at room temperature to determine the effect of room temperature on HCCF and the copper wash. The results are shown in FIG. 4. Lot H was HCCF that was collected and shipped at room temperature. Lot H was treated with ProA wash containing no added copper (0 µM copper) and with ProA wash containing 20 µM Copper. Lot I was treated with ProA wash containing no added copper and with ProA wash containing 50 µM copper. In both cases, the addition of copper to the ProA wash did not substantially lower the partial reduction level, compared to the no copper wash controls. The results for negative controls showed that the initial level of partial reduction (6.8% and 6.4%) was lower than the typical values for negative controls (>10%) which could be due to mixing with air during shipping and some oxidation.

Performing ProA with copper wash demonstrated that level of partial reduction cannot be reduced if HCCF is collected at room temperature. Even increasing the concentration of copper from 20 to 50 µM did not help with mitigating partial reduction and for both case partial reduction after ProA copper wash was 5.9%. One hypothesis is that during harvesting at room temperature the enzymatic reaction/reactions causing partial reduction form more of the partially reduced species that cannot be mitigated using copper wash and therefore in order to reach desired level of partial reduction in ProA pool both copper wash and chilling HCCF at 2-8° C. is required.

To assure robustness of the copper wash step in mitigating partial reduction, experiments were performed on four different lots of 2000 L scale material for Ab A. Purification with ProA including copper wash was performed and the level of partially reduced species in the ProA pool was analyzed by CE-SDS. Results indicated that a 20 µM copper wash resulted in a decreased level of partially reduced species in all Lots tested compared to the negative controls.

The data shown herein demonstrate that in order to achieve a desired level of partial reduction in ProA pool, HCCF would preferably be collected at 2-8° C. and copper wash performed during wash in ProA step. Studies demonstrated that for different HCCF material with various initial level of partial reduction the copper wash brought down level of partial reduction to less than ≤4% in ProA pool. Also, characterization studies demonstrate that the partial reduction in ProA pool is still mitigated to desired level with copper wash at concentrations of 17.6 µM-22.4 µM, with 4 CV, and with 180-210 cm/hr linear velocity during copper wash, and for protein loadings as high as 42 g/L-resin.

Example 4—Effect of Copper Wash on Other Product Quality Attributes

The effect of copper wash on quality attributes such as high molecular weight (HMW) content, light chain and heavy chain (LC and HC), % Basic components and % Acidic components was studied by performing cation exchange chromatography (CEX), size exclusion chromatography (SE-HPLC), and rCE-SDS. Results are shown in Table 1.

TABLE 1

Effect of copper exposure on Antibody A HMW, fragments and charge variants.

| | | RCE HC | RCE HMW | RCE LC | RCE LMW | RCE MMW | RCE NGHC | RCE Post-HC | CEX % Acidic | CEX % Basic | CEX % Main peak | HPLC % HMW | HPLC % LMW | HPLC % Main Peak |
|---|---|---|---|---|---|---|---|---|---|---|---|---|---|---|
| Negative Control | | 65.6 | 0.5 | 32.6 | 0 | 0.3 | 0.6 | 0.4 | 21.2 | 17.2 | 61.6 | 3.3 | 0 | 96.7 |
| 5 µM Copper | 20 min | 65.4 | 0.5 | 32.5 | 0 | 0.4 | 0.6 | 0.6 | 18.1 | 17.6 | 64.3 | 3.2 | 0 | 96.8 |
| 5 µM Copper | 3 hr | 65.5 | 0.5 | 32.5 | 0 | 0.4 | 0.6 | 0.5 | 18.2 | 18.1 | 63.7 | 3.2 | 0 | 96.8 |
| 5 µM Copper | 20 hr | 65.2 | 0.8 | 32.6 | 0 | 0.4 | 0.6 | 0.3 | 19.1 | 17.7 | 63.1 | 3.2 | 0 | 96.8 |
| 25 µM Copper | 20 min | 65.7 | 0.5 | 32.5 | 0 | 0.2 | 0.6 | 0.4 | 18.7 | 17.7 | 63.6 | 3.2 | 0 | 96.9 |
| 25 µM Copper | 3 hr | 65.4 | 0.5 | 32.6 | 0 | 0.5 | 0.6 | 0.4 | 19 | 17.9 | 63.1 | 3.2 | 0 | 96.8 |
| 25 µM Copper | 20 hr | 65.6 | 0.6 | 32.5 | 0 | 0.3 | 0.6 | 0.4 | 19.2 | 17.8 | 63 | 3.1 | 0 | 96.9 |
| 50 µM Copper | 20 min | 65.4 | 0.5 | 32.5 | 0 | 0.5 | 0.6 | 0.4 | 19.2 | 14.1 | 66.6 | 3.1 | 0 | 96.9 |
| 50 µM Copper | 3 hr | 65.5 | 0.6 | 32.5 | 0 | 0.4 | 0.6 | 0.4 | 19 | 17.8 | 63.2 | 3.1 | 0 | 96.9 |
| 50 µM Copper | 20 hr | 65.5 | 0.6 | 32.5 | 0 | 0.4 | 0.6 | 0.4 | 19 | 17.7 | 63.3 | 3.2 | 0 | 96.8 |

Abbreviations:
RCE = reduced CD-SDS;
CEX = cation exchange chromatography;
HPLC = high performance liquid chromatography;
MMW = medium molecular weight;
NGHC = non-glycosylated heavy chain;
Post-HC = post heavy chain species In summary, the data in Table 1 indicate that copper wash has no effect on HMW content (SEC results), or LC and HC (rCE-SDS result) and % Basic components (CEX result). However, it did help decrease the level of % Acidic components and increase the % Main peak based on CEX results which is consistent with the decrease in level of partially reduced species (which co-elute with other acidic components) and increase in level of desired product.

Figure 5:
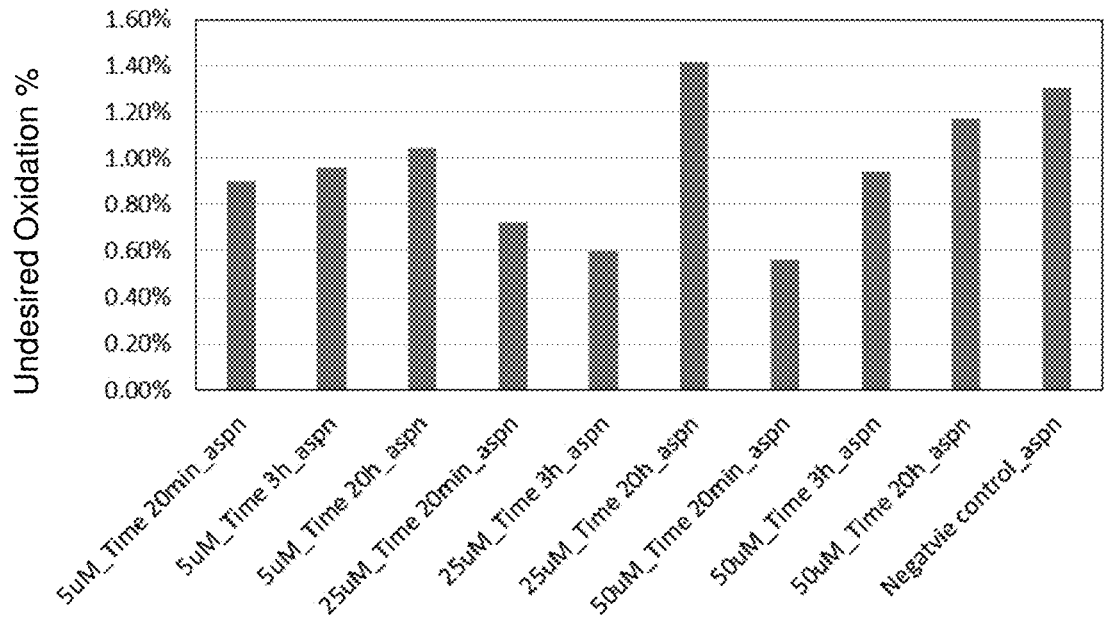
FIG. 5 shows the effect of copper wash on undesirable oxidation.

Experiments were also performed to study the possibility of undesired side oxidations due to exposure to copper. FIG. 5 shows that no undesirable oxidation was observed under the conditions tested Results indicated that the copper wash does not cause any undesired changes in tested product quality attributes.

Example 5—Effect of Higher Loading and Copper Concentration

Copper wash characterization was performed to demonstrate the robustness of the copper wash for mitigation partial reduction for Ab-A. Table 2 shows the parameters that were tested and they were studied in two sets of experiments.

TABLE 2

Process Parameters Identified for Testing

| Process Parameter | Set-Point | Range Tested |
|---|---|---|
| Protein Loading [g/L-resin] | 30 | 19-42 |
| Copper Concentration during Copper Wash (µM) | 20 | 17.6-22.4 |
| Copper Wash Linear Velocity (cm/hr) | 180 | 150-210 |

Figure 6:
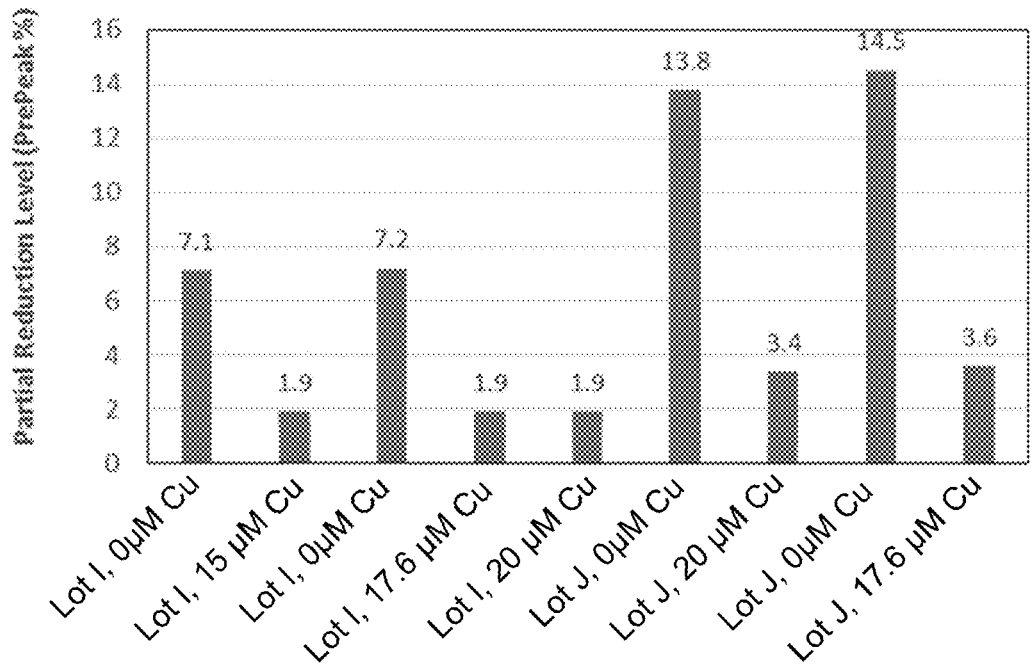
FIG. 6 characterizes levels of copper below 20 uM (process robustness)

For this experiment ProA column was loaded at higher end of normal operating range (38 g/L-resin), copper wash was performed at set-point for linear velocity (180 cm/hr), and copper concentrations of 17.6 µM and 15 µM were studied to cover the lower end of characterization range (and even lower down to 15 µM). FIG. 6 shows the result of this experiment. Previous data included concentrations up to 50 µM which covers ranges higher than the upper end of copper concentration characterization range.

The result from the experiments indicated that even at lower end of copper concentrations characterization range (17.6 µM) the on column re-oxidation is capable to decrease level of partial reduction to less than 4% in ProA pool.

Example 6—Effect of High Loading an Linear Velocity

Figure 7:
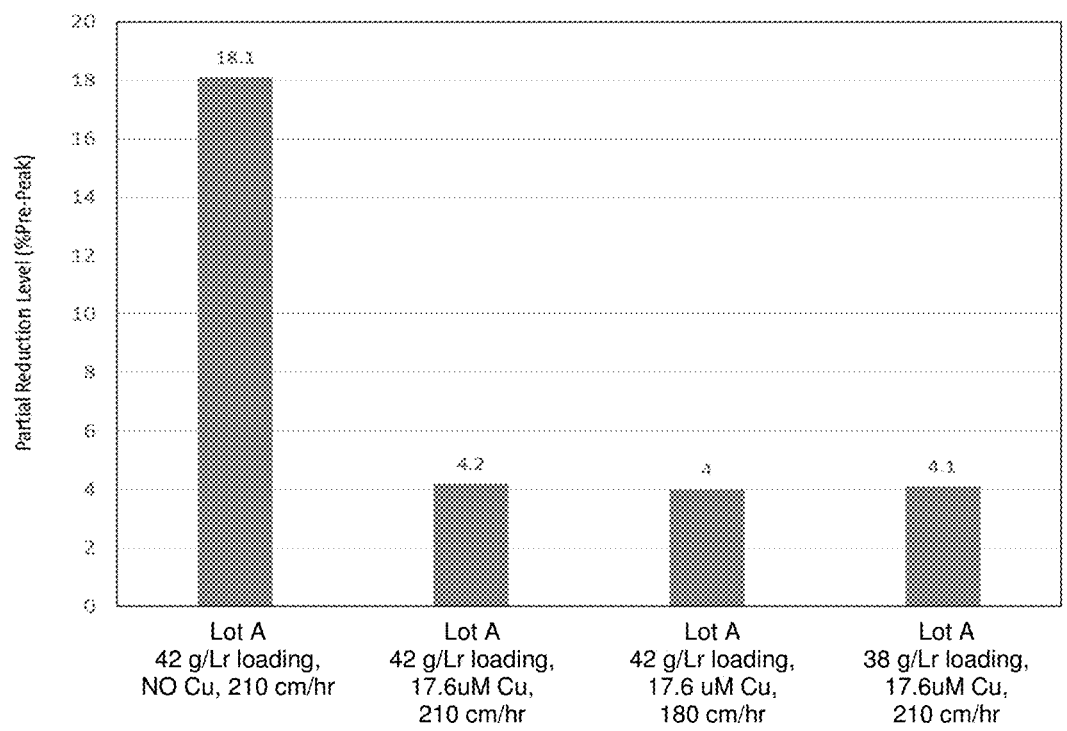
FIG. 7 characterizes the effect of protein loading and copper wash linear velocity on partial reduction level decrease in ProA pool.

The second set of experiments was focused on understanding the effect of column loading and copper wash linear velocity (i.e. exposure time) on copper wash effectiveness. For these experiments frozen HCCF was used and 17.6 µM copper wash was performed. Two levels of loading (38 and 42 g/L-resin) and two linear velocities for copper wash (180 and 210 cm/hr) were studied to cover lower end of characterization range for exposure time (i.e. copper wash linear velocity) and highest end of characterization range for loading. FIG. 7 shows the results from these experiments where the initial level of partial reduction without any copper wash is 18% and for 42 g/L-resin loading and copper wash linear velocity of 210 cm/hr (exposure time of 25 min), the 17.6 µM copper wash is able to bring down the level of partial reduction to 4.2%.

Results also show that 17.6 µM copper wash with flow rate as high as 210 cm/hr and loading as high as 42 g/L resin is still effective in bringing the partial reduction down to around 4%.

Example 7—Re-Oxidation of AbP-1

The experiments described in this Example 2 were repeated using an antigen binding protein in the BiTE format (AbP-1) in place of Ab-A.

Materials/Methods:

MabSelect SuRe resin was used for all the experiments and experiments were performed on one of two ProA columns of varying diameters. ProA columns were packed to 25±2 cm or 20±2 cm bed height and were tested for integrity. pH and conductivity were monitored using in-line probes.

Load material was harvested cell culture fluid (HCCF) from representative cell culture runs ranging in scale from 2 L to 50 L.

Operation was at room temperature. HCCF was loaded to column at room temperature.

A solution (25 mM tris, 100 mM NaCl, pH 7.4) comprising copper sulfate at various concentrations (i.e., 0 µM, 20 µM, 40 µM and 60 µM, 200 µM and 2 mM) used.

A copper wash at various concentrations (e.g., 0 µM, 20 µM, 40 µM and 60 µM) was applied to a MabSelect column at a linear velocity of 100 cm/hr for 20 column volumes.

Figure 8:
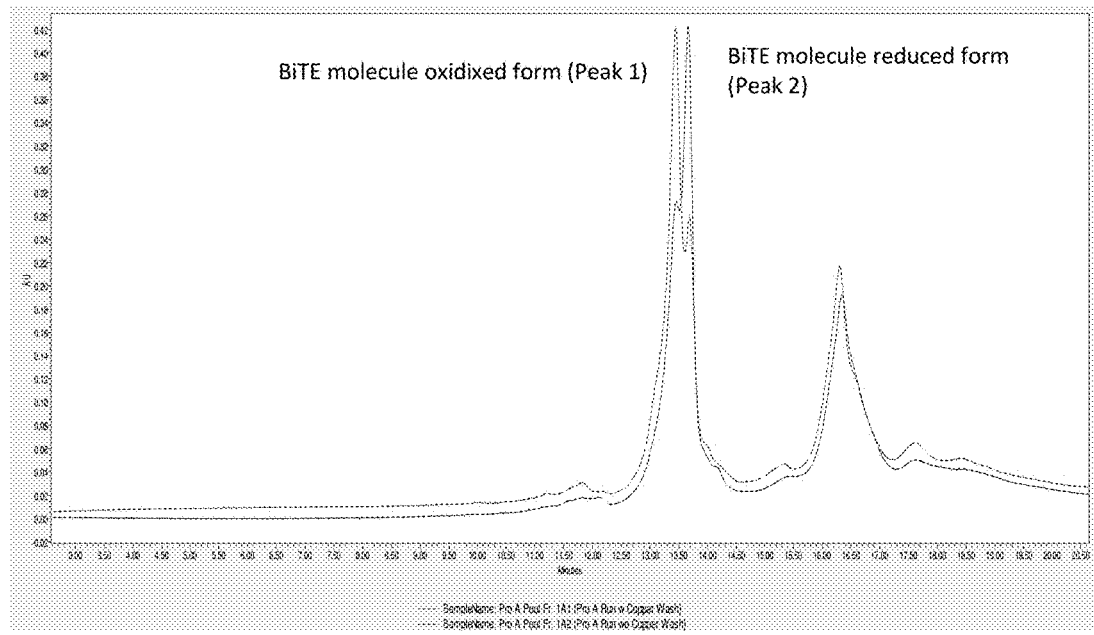
FIG. 8 shows the effect of copper wash (20 µM) during ProA on level of partial reduction of antigen binding protein AbP-1 in ProA pool.
Figure 9:
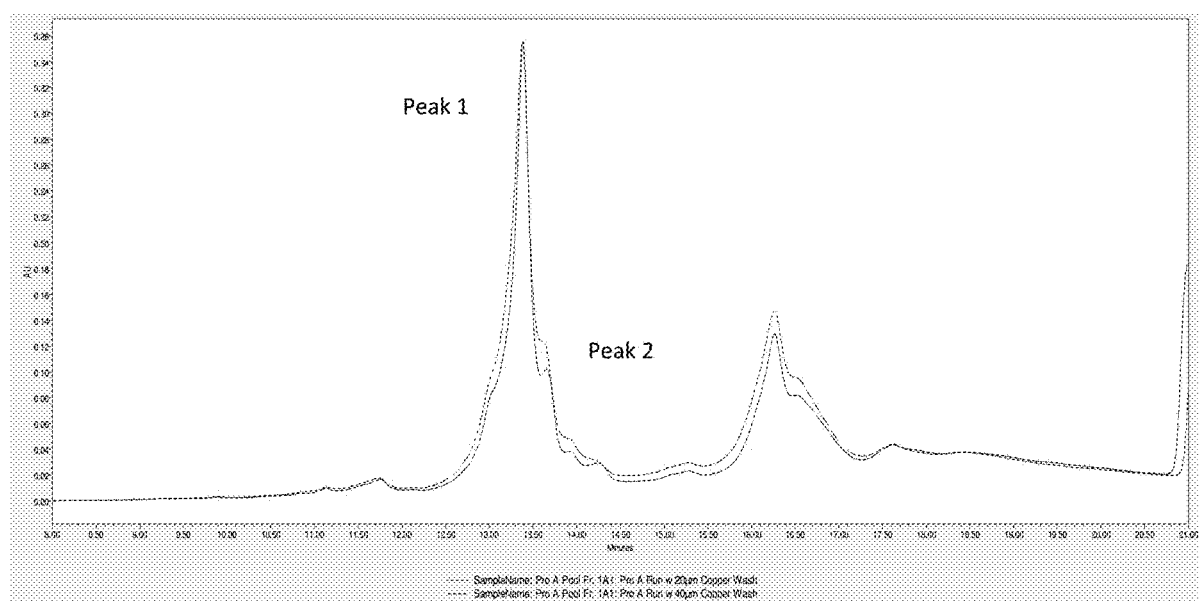
FIG. 9 shows the effect of copper wash (40 µM) during ProA on level of partial reduction of antigen binding protein AbP-1 in ProA pool.

The length of the exposure time to wash was 24 minutes, controlled by the linear velocity of flow during wash step and the length of the wash step (i.e. number of column volumes for the wash). As shown in FIG. 8 and FIG. 9, the copper addition (at 20 µM and 40 µM) during the ProA wash were both effective in reducing the level of partially-reduced species with the 40 µM copper wash being the most effective in reducing the level of partial reduction when compared to the control (0 µM copper wash). The 60 µM copper wash also reduced the level of partial reduction (data not shown). The level of partially-reduced species of AbP-1 decreased as the concentration of copper in the copper wash increased from 20 µM to 60 µM.

Example 8—Effect of Alternative Affinity Column Combined with Copper Wash

Figure 10:
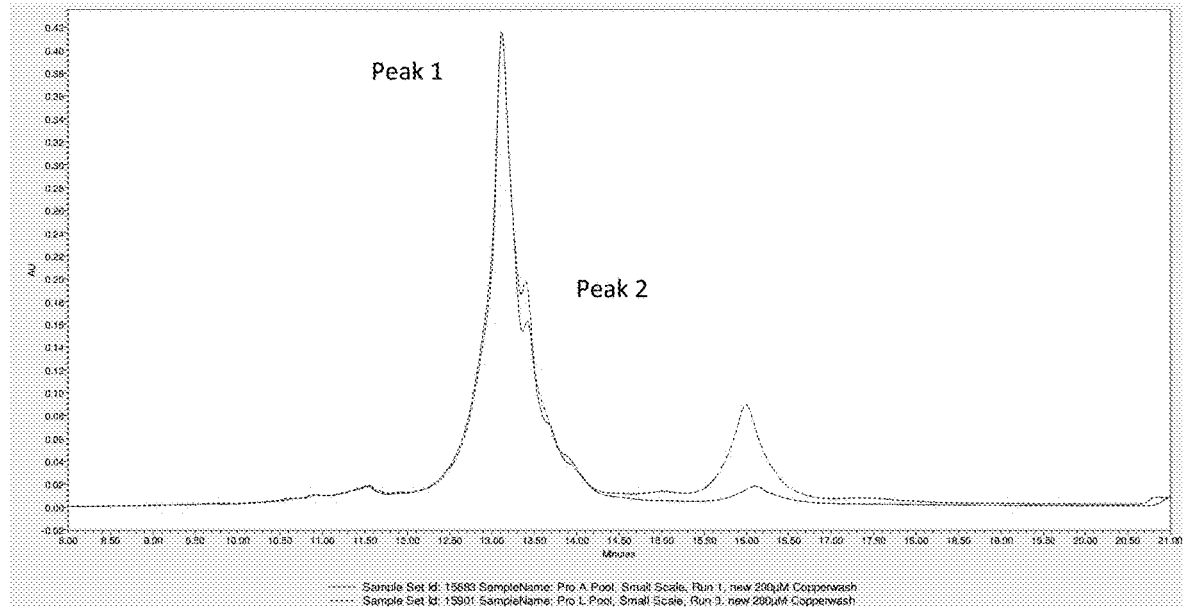
FIG. 10 shows the effect of copper wash (200 µM) during ProA on level of partial reduction of antigen binding protein AbP-1 in ProL pool.

The experiment in Example 7 was repeated using a Protein L column in place of the Protein A column. AbP-1 was loaded onto the Protein L column as described above with respect to the Protein A column. A 200 µM copper wash was applied to a Protein L column as described above at a linear velocity of 125 cm/hr (100 cm/hr for a 30 cm bed height) for 4 column volumes. As shown in FIG. 10, the 200 µM copper wash resulted in significantly reduced the level of partially-reduced species when compared to the control (0 µM copper wash).

Example 9—Effect of Cysteamine on Re-Oxidation of an Antigen-Binding Protein

Figure 11:
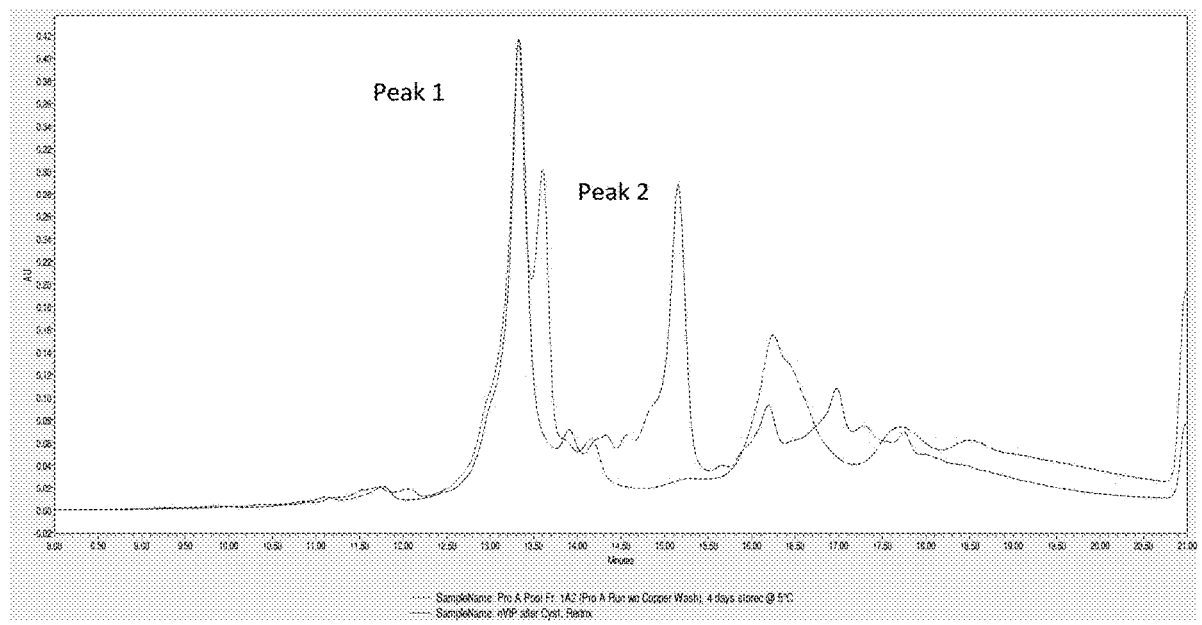
FIG. 11 shows the effect of cysteamine on level of partial reduction of antigen binding protein AbP-1 in a sample collected from a ProA column.

The following Example describes the reoxidation of an antigen-binding protein with a redox agent other than copper. In this Example, the reoxidation occurs downstream of the ProA affinity column. AbP-1 ProA pool was collected and mixed with a redox solution of cystamine and cysteamine (0.8M cystamine, 2HCl, 0.2M cysteamine HCL in 1M Tris), adjusting the pH of the mixture to 7.9 and stirring for a period of time. Cation Exchange Chromatography (CEX) was used to monitor the reaction progression (typically complete in 1-2 hours). Cysteamine was purged from the partially over-reduced AbP-1 solution by buffer exchange into 20 mM sodium acetate, pH 5.0. The resulting partially over-reduced and cysteamine-free AbP-1 (3-12 mg/mL) was reoxidized by addition of 4-7 equiv. of 4 mM dehydroascorbic acid, 0.5 M aq. $Na_2HPO_4$ to pH 7.0-7.5 followed by incubation at 2-8° C. The reoxidation progress was monitored by Reversed Phase HPLC. As shown in FIG. 11, no double peak is detectable after the addition of cysteamine.

---

What is claimed is:

1. A method of re-oxidizing a therapeutic protein comprising at least one di-sulfide bridge, said method comprising:
   (a) subjecting a load composition comprising the therapeutic protein to an affinity chromatography column or membrane; and
   (b) washing the affinity chromatography column or membrane, wherein the wash comprises a solution comprising copper at a concentration ranging from 2 µM to 50 µM to produce a flow-through composition,
   wherein a decreased level of partially-reduced therapeutic protein species is present in the flow-through composition compared to the load composition.

2. The method of claim 1 wherein the therapeutic protein is an antigen-binding protein.

3. The method of claim 1, wherein the affinity chromatography column is a Protein A affinity column.

4. The method of claim 1 wherein the affinity chromatography column is a Protein L affinity column.

5. The method of claim 1, wherein the copper in the solution is copper sulfate.

6. The method of claim 1, wherein the copper in the solution is present in an amount of approximately 20 µM.

7. The method of claim 1, wherein the copper in the solution is present in an amount of approximately 40 µM.

8. The method of claim 1, wherein the conditions in step (b) comprise washing at room temperature.

9. The method of claim 1, further comprising incubating the load composition comprising the therapeutic protein at a temperature of approximately 2 to 8° C. before step (a).

10. The method of claim 7, wherein the load composition is incubated for 1-3 days at a temperature of approximately 2 to 8° C. and wherein the washing conditions in part (b) are conditions sufficient to achieve at least partial re-oxidation of the therapeutic protein.

11. A method of re-oxidizing a therapeutic protein comprising at least one reduced di-sulfide bridge, said method comprising:
   (a) incubating a load composition comprising the therapeutic protein at a temperature of approximately 2 to 8° C.;
   (b) subjecting the load composition to an affinity chromatography column or membrane; and
   (c) washing the affinity chromatography column or membrane, wherein the wash comprises a solution comprising copper in an amount ranging from 2 µM to 50 µM to produce a flow-through composition,
   wherein a decreased level of partially-reduced therapeutic protein species is present in the flow-through composition compared to the load composition.

12. The method of claim 11, wherein the therapeutic protein is an antigen-binding protein.

13. The method of claim 11, wherein the affinity chromatography column is a Protein A affinity column.

14. The method of claim 11, wherein the load composition is incubated for 1-3 days at a temperature of approximately 2 to 8° C. and wherein the washing conditions in part (c) are conditions sufficient to achieve at least partial re-oxidation of the therapeutic protein.

15. The method of claim 11, wherein the copper in the re-oxidizing solution is copper sulfate.

16. The method of claim 11, wherein the copper in the re-oxidizing solution is present in an amount of approximately 20 µM.

17. The method of claim 11, wherein the copper in the re-oxidizing solution is present in an amount of approximately 40 µM.

18. The method of claim 11, wherein the conditions in step (c) comprise washing at room temperature.

19. The method of claim 11, wherein the conditions in step (c) comprise washing at a linear velocity of approximately 180-210 cm/hr.

20. The method of claim 11, wherein the conditions in step (c) are sufficient to lower the amount of partially-reduced antigen-binding proteins in the flow-through composition to less than approximately 5% compared to more than approximately 16% in the load composition.

21. The method of claim 11, wherein said conditions in step (c) are sufficient to lower the amount of partially-reduced antigen-binding proteins in the flow-through composition to less than approximately 4% compared to more than approximately 5% in the load composition.

22. The method of claim 11, further comprising the step of freezing and thawing the load composition prior to step (a).

23. The method of claim 11, further comprising the step of recovering the therapeutic protein.

24. The method of claim 2, wherein the antigen-binding protein is an antibody.

25. The method of claim 2, wherein the antigen-binding protein is BiTE protein.

26. The method of claim 24 or 25, wherein the antigen-binding protein is recombinantly produced.

27. The method of claim 26, wherein the antigen-binding protein is recombinantly produced in a Chinese Hamster Ovary (CHO) cell.

28. The method of claim 1 or claim 11, wherein the load composition is a harvested cell culture fluid (HCCF).

29. The method according to claim 24, wherein the antibody is an IgG1 or IgG2 antibody.

30. The method according to claim 29, wherein the antibody is an IgG1 antibody with a Kappa light chain.

31. The method according to claim 29, wherein the antibody is an IgG1 antibody with a Lambda light chain.

32. The method according to claim 1, wherein the therapeutic protein binds an antigen selected from the group consisting of RANKL, tumor necrosis factor alpha, epidermal growth factor receptor, CD20, calcitonin gene-related peptide, sclerostin, and platelet glycoprotein IIb/IIIa.

33. The method according to claim 24, wherein the antibody is abciximab, adalimumab, alemtuzumab, basiliximab, belimumab, bevacizumab, brentuximab vedotin, canakinumab, cetuximab, certolizumab pegol, daclizumab, denosumab, eculizumab, efalizumab, gemtuzumab, golimumab, ibritumomab tiuxetan, infliximab, ipilimumab, muromonab-CD3, natalizumab, nivolumab, ofatumumab, omalizumab, palivizumab, panitumumab, ranibizumab, rituximab, tocilizumab, tositumomab, trastuzumab, ustekinumab, vedolizumab, or a biosimilar of any of the foregoing.

34. The method according to claim 25, wherein the BiTE molecule is an anti-CD33 and anti-CD3 BiTE molecule, anti-BCMA and anti-CD3 BiTE molecule, anti-FLT3 and anti-CD3 BiTE, anti-CD19 and anti-CD3 BiTE, anti-EGFRvIII and anti-CD3 BiTE molecule, anti-DLL3 and anti-CD3 BiTE, anti-CLDN18.2 and anti-CD3 BiTE molecule, anti-EpCAM and anti-CD-3 BiTE molecule, anti-CEA and anti-CD3 BiTE molecule, anti-PSMA and anti-CD3 BiTE molecule, blinatumomab (BLINCYTO), or solitomab.

35. The method according to claim 2 or claim 12, wherein the antigen-binding protein comprises an antigen-binding region comprising an amino acid sequence selected from the group consisting of SEQ ID NOS: 1-8.

* * * * *